(12) United States Patent
Fischer et al.

(10) Patent No.: US 12,029,471 B2
(45) Date of Patent: Jul. 9, 2024

(54) HF-SURGICAL PREPARATION INSTRUMENT WITH FLUID CHANNEL

(71) Applicant: Erbe Elektromedizin GmbH, Tuebingen (DE)

(72) Inventors: Klaus Fischer, Nagold (DE); Markus Enderle, Tuebingen (DE); Achim Brodbeck, Metzingen (DE); Alexander Neagos, Reutlingen (DE); Andreas Fech, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 836 days.

(21) Appl. No.: 16/577,085

(22) Filed: Sep. 20, 2019

(65) Prior Publication Data

US 2020/0093537 A1 Mar. 26, 2020

(30) Foreign Application Priority Data

Sep. 26, 2018 (EP) .................................... 18196945

(51) Int. Cl.
*A61B 18/14* (2006.01)
*A61B 17/3203* (2006.01)

(52) U.S. Cl.
CPC ...... *A61B 18/1442* (2013.01); *A61B 17/3203* (2013.01); *A61B 18/1482* (2013.01);
(Continued)

(58) Field of Classification Search
CPC ...... A61B 17/3203; A61B 2017/32035; A61B 18/1402; A61B 18/1442; A61B 18/1482;
(Continued)

(56) References Cited

U.S. PATENT DOCUMENTS 5,366,490 A 11/1994 Edwards et al.
5,382,247 A 1/1995 Cimino et al.
(Continued)

FOREIGN PATENT DOCUMENTS

CN 107438411 A 12/2017
GB 2535305 A 8/2016
(Continued)

OTHER PUBLICATIONS

Extended European Search Report issued on Mar. 26, 2019, in corresponding European Patent Application No. 18196945.2 (7 pages).

(Continued)

*Primary Examiner* — Khadijeh A Vahdat
(74) *Attorney, Agent, or Firm* — Fitch, Even, Tabin & Flannery LLP

(57) ABSTRACT

A preparation instrument comprising an HF-instrument with an electrode that is partially insulated by means of an insulating body, which is combined with a fluid applicator having a channel arranged in the insulating body for the application of a fluid to or into tissue. In some embodiments of the preparation instrument, the electrode is a spatula electrode which is inserted in the insulating body that does not cover sections of the surface of the electrode so that these sections may be in contact with the tissue. The insulating body preferably forms the channel wall that delimits the channel. The insulating body and the electrode may be flexible in order to adapt the form of the insulating body and the electrode, together, to the surgical task.

16 Claims, 7 Drawing Sheets

(52) U.S. Cl.
CPC ............... *A61B 2017/32035* (2013.01); *A61B 2018/1422* (2013.01); *A61B 2018/1452* (2013.01)

(58) Field of Classification Search
CPC ........... A61B 2018/00029; A61B 2018/00083; A61B 2018/00601; A61B 2018/1412; A61B 2018/1422; A61B 2018/1452; A61B 2018/1465; A61B 2218/002; A61B 2218/003; A61B 2218/005; A61B 2218/006
See application file for complete search history.

(56) References Cited

U.S. PATENT DOCUMENTS

| | | | |
|---|---|---|---|
| 5,421,819 A | 6/1995 | Edwards et al. | |
| 5,697,281 A * | 12/1997 | Eggers | A61B 18/1206 604/114 |
| 6,391,027 B1 * | 5/2002 | Farin | A61B 18/14 606/45 |
| 6,723,094 B1 | 4/2004 | Desinger | |
| 7,255,696 B2 | 8/2007 | Goble et al. | |
| 8,177,783 B2 * | 5/2012 | Davison | A61B 18/1402 606/41 |
| 2003/0073993 A1 * | 4/2003 | Ciarrocca | A61B 18/1402 606/41 |
| 2006/0111709 A1 | 5/2006 | Goble et al. | |
| 2006/0264929 A1 | 11/2006 | Goble et al. | |
| 2008/0058821 A1 * | 3/2008 | Maurer | A61B 18/1402 606/50 |
| 2008/0071267 A1 | 3/2008 | Wang et al. | |
| 2011/0098704 A1 * | 4/2011 | Long | A61B 90/08 606/49 |
| 2011/0118582 A1 * | 5/2011 | De la Rama | A61B 90/06 600/374 |
| 2011/0224669 A1 * | 9/2011 | Podany | A61B 18/1233 606/49 |
| 2013/0041363 A1 | 2/2013 | Van Wyk et al. | |
| 2014/0039493 A1 | 2/2014 | Conley et al. | |
| 2015/0297284 A1 | 10/2015 | McClurken et al. | |
| 2016/0374751 A1 * | 12/2016 | Davies | A61B 18/1477 606/48 |

FOREIGN PATENT DOCUMENTS

| | | |
|---|---|---|
| KR | 10-2018-0069810 A | 6/2018 |
| RU | 2295931 C2 | 3/2007 |
| RU | 2542372 C2 | 2/2015 |
| RU | 2577811 C2 | 3/2016 |
| WO | 95/19739 A1 | 7/1995 |
| WO | 2016/073164 A1 | 5/2016 |

OTHER PUBLICATIONS

Shegu Gilbert et al., Modified carbodissection: A technique for harvesting the internal mammary artery, Multimedia Manual of Cardio-Thoracic Surgery, Oct. 29, 2017, https://mmcts.org/tutorial/830#additionalinfo, accessed on Sep. 9, 2019 (11 pages).
Indian Office Action dated Aug. 2, 2022, in corresponding Indian Application No. 201914038118, 4 pages.
Russian Office Action and Search Report dated Jul. 28, 2022, in corresponding Russian Application No. 2019129491/14(058077), 11 pages.
Chinese Office Action and Search Report dated Jul. 20, 2022, in corresponding Chinese Application No. 2019109170123, 19 pages.
Japanese Patent Office, Notice of Reasons for Refusal for Japanese Application No. 2019-173750, dated Feb. 13, 2023, 15 pages.
Japanese Patent Office, Notification of Patent Right for Japanese Application No. 2019-173750, dated Jun. 13, 2023, 6 pages.
Korean Intellectual Property Office (KIPO); Notice of Preliminary Rejection in correspondence Korean Patent Application No. 10-2019-0117957, dated Mar. 20, 2024; 12 pages.

* cited by examiner

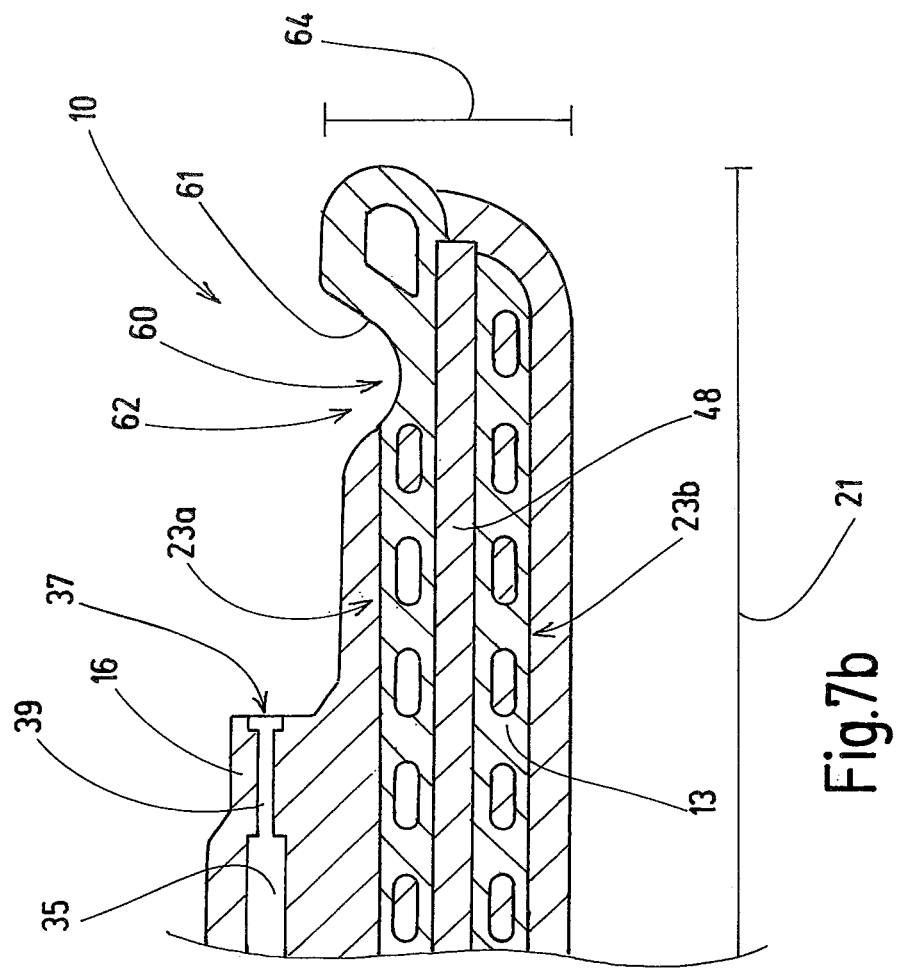
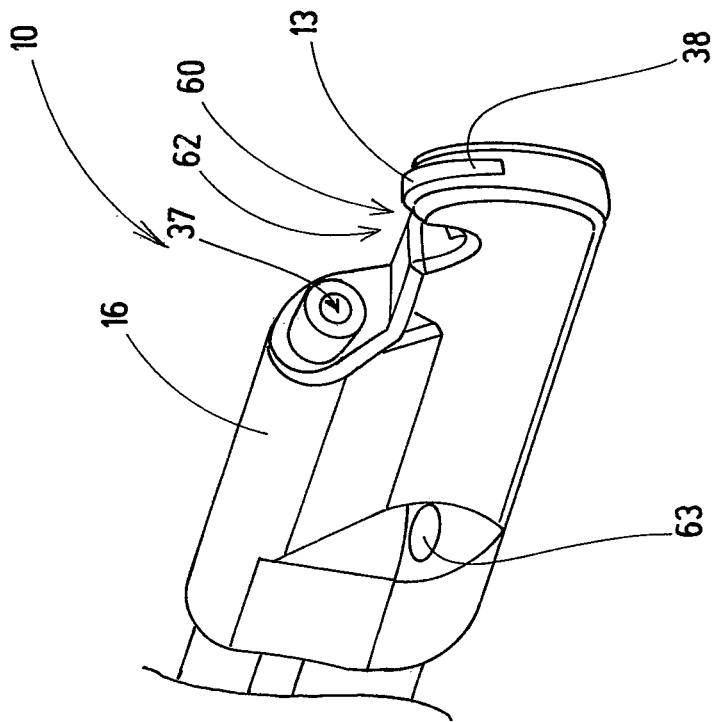

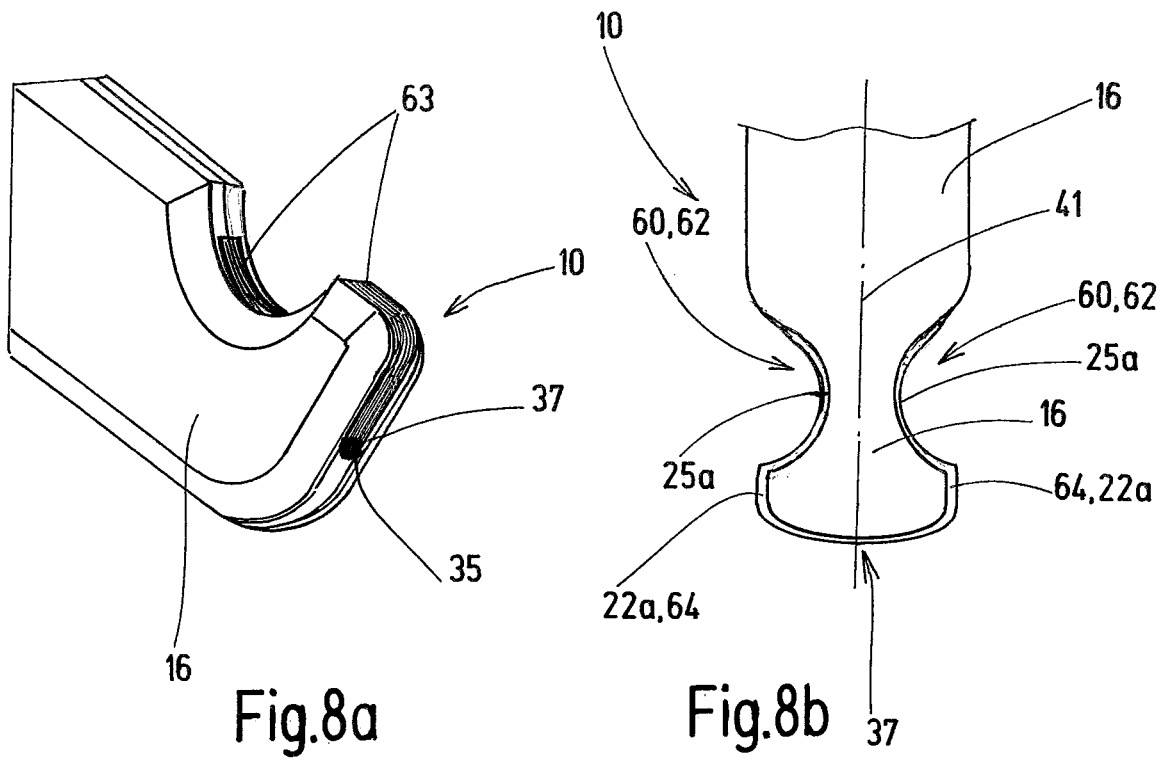
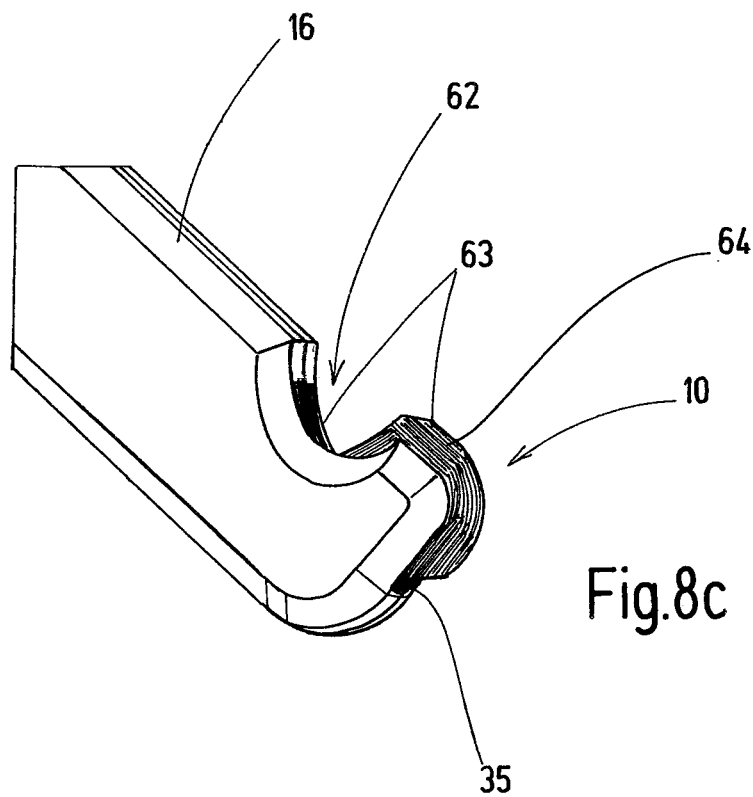

HF-SURGICAL PREPARATION INSTRUMENT WITH FLUID CHANNEL

RELATED APPLICATION(S)

This application claims the benefit of European Patent Application No. 18196945.2, filed Sep. 26, 2018, the contents of which are incorporated herein by reference as if fully rewritten herein.

TECHNICAL FIELD

The invention relates to an HF-surgical preparation instrument.

BACKGROUND

In addition to the strictly mechanical preparation with forceps and clamps, diathermic procedures (high-frequency (HF) surgical procedures) are nowadays the means of choice. Presently, non-insulated spatula or hook electrodes are used for the preparation of tissue structures. In contrast, partially insulated electrodes are used in particular when a thermal damage of the structures to be spared, or adjacent structures, is to be as minimal as possible. In the case of known preparation instruments, precise and safe work can be made difficult due to a restricted view of the surgical site, for example as a result of oozing blood, carbonized blood and tissue, as well as overlays over the instrument tip (the active region) due to "flowing" tissue.

Publication US 2006/0 111 709 A1 discloses an electrosurgical instrument, which comprises a hook electrode, wherein the cooling fluid can be conveyed from a reservoir, through the instrument body to the electrode tip, through an opening in the electrode, and from there into a return channel back to the reservoir. Thus the electrode can be cooled.

Publication WO 95/19 739 A discloses an electrosurgical instrument with an electrode having a free end, wherein the electrode is enclosed by a coat of electrically insulating material up to before the end, wherein—in a section of the coat that adjoins the end—openings are contained in the coat that extend from the electrode to the surface of the coat in order to apply an HF-output to the tissue through the openings.

Publication WO 2016/0731 64 A1 shows an electrosurgical instrument with a non-insulating electrode that encloses a channel through which gas is expelled from an opening at the end of the electrode in order to displace oxygen from the end of the electrode.

Website http://mmcts.org/tutorial/830#additionalinfo discloses an instrument which combines an electrosurgical instrument and an instrument for dispense a mixture of $CO_2$ and saline, wherein the electrosurgical instrument and the additional instrument are connected by threads.

Considering this prior art, it is the object of the present invention to provide an improved instrument.

SUMMARY

This object is achieved with an HF-surgical preparation instrument, as well as with a device, as described herein.

The HF-surgical preparation instrument (hereinafter also referred to as the preparation instrument or instrument) comprises an electrode for applying an HF-output to tissue, wherein the surface sections of the electrode are electrically and thermally insulated in outward direction by an insulating body. A channel is provided inside the insulating body, said channel being adapted to dispense a fluid such as a gas, a fluid and/or aerosol, onto or into the tissue or between tissue structures. The channel can be or is connected to a fluid source, for example a gas source, fluid source and/or aerosol source.

Preferably, the instrument is a monopolar HF-instrument. The HF-generator that supplies the instrument is connected to a separate neutral electrode which is in electrical contact with a large area of the patient.

By means of the HF-surgical preparation instrument, the gas, fluid and/or aerosol can be dispensed in or next to a region of action of the HF-output. Accordingly, the preparation instrument forms a fluid applicator.

Within the meaning of this patent application, an aerosol is understood to be a mixture of a gas and a liquid, in particular liquid droplets suspended in a gas.

With the inventive instrument it is possible to prepare tissue in a gentle and precise manner. Here, preparation is understood to mean the exposure and presentation of vulnerable anatomical structures such as, e.g., nerves or vessels, by blunt separation/displacement and/or sharp separation. In HF-surgical preparation, for example, an HF-spatula is used for detaching specific tissue structures such as vessels, nerves and organs, at least partially—away from the tissue composite. During this step, it is imperative that there will be no inadvertent thermal damage to sensitive (to be prepared) or adjacent structures. The instrument according to the invention ensures that a contact surface between the tissue and the HF-electrode is known or can be controlled at any time. By moving away or displacing tissue, tissue structures, tissue remainders, body fluids or other fluids or vapors by means of the gas, fluid and/or aerosol applicator function of the inventive instrument, the surgeon can at all times make the individual tissue boundaries clearly recognizable.

Preferably, the channel extends next to the electrode—with or without a distance therefrom. Alternatively, the electrode may contain the channel. Preferably, however, the insulating body delimits the channel. This means that the insulating body forms the channel wall—at least partially. For example, it is possible to omit a small tube in the insulating body in this section, wherein the small tube contains the channel section. Preferably, the channel extends within the wall thickness of the insulating body. Preferably, the electrode extends at a distance from the channel along the channel. Preferably, the electrode is not arranged in the channel and, preferably, does not extend into the channel, so that the channel does not enclose the electrode—viewed in a cross-sectional plane through the channel.

Preferably, the channel has a nozzle section at the end section, in which the cross-section, in particular the diameter of the channel, tapers. Preferably, the nozzle section is delimited by the insulating body. This means that the insulating body forms the wall of the nozzle section of the channel.

The distal end section (instrument tip), in particular the electrode and the insulating body, is preferably flexible in order to adapt the form of the insulating body and of the electrode to the treatment task. If the external force used for bending is taken away, the desired form of the end section of the insulating body is preferably maintained. The orientation of the nozzle of the channel relative to the electrode tip preferably remains maintained. Preferably, the end section can be bent manually. If the end section can be bent into the desired form, this promotes a precise and tissue-sparing preparation such as, for example during the removal of a vessel.

Due to the insulation, the electrical contact area between the electrode and the tissue can be set to a defined and narrowly limited region. As a result of this, the energy introduced into the tissue decreases, on the one hand. Due to the limited effective range, the lateral damage, as well as the risk of inadvertent thermal stress on the surrounding tissue is minimized, on the other hand.

If the insulating body delimits the channel, in particular if the insulating body delimits the end section of the channel that allows, at the opening of the channel, the dispensing of the aerosol or the fluid into the effective region of the instrument, this has the result that, if the instrument is bent, the orientation (angle) of the end section of the channel remains maintained relative to the orientation of the distal end section of the electrode.

Preferably, the electrode is not arranged in a channel that would be adapted for conveying a fluid stream. The electrode may be arranged in a recess of the insulating body. The electrode may completely fill the recess or at least close the opening in the recess.

In preferred embodiments, the electrode has the shape of a spatula. This means that the electrode comprises at least one spatula-shaped distal end section. Together with an HF-spatula, the instrument forms a spatula-shaped electrode. In preferred embodiments, the electrode has a wire-shaped section that preferably extends along the longitudinal extent of the electrode. Alternatively, the electrode may have, for example, an elongated slit or recess that may extend, for example, from the proximal end of the electrode to the end section of the electrode, wherein a wire-shaped body, preferably a metal body, is arranged in the slit or recess. Preferably, the wire-shaped body is connected to the electrode, preferably welded to the electrode sheet metal. The wire-shaped body is not necessarily adapted to conduct current, but may also be arranged for strictly mechanical purposes in order to allow bending the end section of the instrument and holding the end section in the desired bent form. Thus the wire-shaped body may be adapted to output electrical power into the electrode and/or be adapted to mechanically stabilize the electrode. In order to be able to prepare the preparation instrument in a particularly precise and insulated manner, a thin electrode is desirable. As the thickness of the electrode decreases, however, the mechanical stiffness of the electrode decreases. If necessary, this may be compensated for by the wire-shaped body or section. Moreover, the wire-shaped body or section can improve the removal of thermal energy from the tip of the preparation instrument through the end section of the preparation instrument.

If, as in the exemplary embodiments of the instrument according to the invention, an HF-spatula is combined with a fluid applicator (hybrid spatula), any thermal damage of the structures can largely be reduced by this, and the view onto the surgical site can be improved. The instrument allows the application or introduction of a fluid, for example a gas, a fluid or a mixture of both to the tissue in order to displace the tissue or to elevate the tissue. As a result of this, individual tissue structures or their boundaries can be displayed more distinctly. Furthermore, by dispensing fluid, it is possible to rinse away or displace body fluids such as, among other things, blood, tissue remainders, vapor, smoke and the like.

During the application of a fluid (in particular a liquid) with a high power density, said fluid penetrates the tissue and accumulates in the connective tissue-like boundary regions between the target structure and the adjacent structures, so that these are pushed apart, and an enlarged (safety) distance for the manipulation with the instrument is formed (mechanical and thermal protection).

If, as opposed to this, a fluid stream (in particular, a gas) is directed from a certain distance at the tissue with relatively low intensity, displacement effects (deformation) occur on the tissue due to the action of force of the streaming fluid. Due to different mechanical properties, e.g., the elasticity of the individual tissue structures, such effects may be more or less pronounced. Consequently, it is possible, for example, to more clearly limit stiffer structures such as vessels with respect to the surrounding softer tissue such as, for example, fat.

Furthermore, by applying an aerosol spray, it is possible to implement a cooling of the surgical site and thus implement an additional protection against thermal damage due to HF-exposure. Inasmuch as an aerosol reduces the smoke formation during the HF-application, the view on the surgical site can be clearly improved.

In order to aid the user in avoiding a harmful effect of the fluid, in particular aerosol, and/or in preventing in particular the introduction of gas or aerosol into the tissue, e.g., a blood vessel, the outlet of the channel, specifically the outlet of the nozzle, can be set back preferably proximally from the distal end of the electrode. Consequently, in particular a placement of the outlet of the channel on the tissue is prevented. In preferred embodiments, the distal end of the channel on which the outlet is provided, is set back from the distal end of the electrode by including 2 mm to including 10 mm. In the embodiments, the distal end of the channel or the outlet of the channel may be set back from the distal end of the electrode, for example, between 2 and 4 mm, in proximal direction.

The spatula-shaped electrode has an upper side and an underside that are connected to the edges of the electrode, via one lateral surface, respectively. The distal end section of the channel is preferably located in a plane, which is spanned by the longitudinal axis of the electrode or the longitudinal axis of the wire-shaped section or body or the longitudinal section of the electrode or the insulating body, respectively, that is arranged in the direction of flow of the fluid from the outlet of the channel downstream of the outlet of the channel, and by a surface normal of the upper side or the underside of the electrode. The angle of orientation (azimuth) between the distal end section of the channel and the longitudinal extent direction of the electrode and/or of a wire-shaped body and/or of the longitudinal axis of the section of the electrode or insulating body that is arranged in the direction of flow out of the outlet of the channel downstream of the outlet of the channel is particularly preferred, namely 0°. Alternatively, the azimuth may be 0°±10° or 0°±5° or comprise a different angular range. The azimuth is preferably measured in a plane, in which the spatula-shaped electrode is located or can be bent in such a manner that it is located in this plane, and/or in which a section of the insulating body or the electrode is located, said section being arranged between the outlet of the channel and the distal end of the insulating body and/or the electrode.

In the embodiments of the instrument, the electrode does not have an opening through which the gas, fluid and/or aerosol is conveyed. In particular, the electrode preferably does not have a channel extending through the electrode, which channel would convey a gas, an aerosol or a fluid during operation.

The electrode of the instrument according to the invention preferably projects distally from the insulating body. In this manner, a transfer of HF-output into the tissue also originates laterally from the electrode via the not insulated section.

The region of the upper side and/or the region of the underside of the electrode that is preferably not covered by the insulating body is preferably arcuate or encloses the insulating body in an arcuate manner (in plan view). The not covered region may end next to a section of the insulating body that is arranged between the outlet of the channel and the distal end of the instrument. Thus, the not covered region ends—from the viewpoint of the user—distal to the outlet. Alternatively, the not covered region may end next to the section of the insulating body that contains the channel. Thus the not covered region ends proximal to the outlet. If the not covered region ends proximal to the outlet of the channel, the exposed region of the electrode extends in proximal direction next to the outlet beyond the outlet of the channel.

The noncoverage by the insulating body can be restricted to those areas of the electrode whose next edge surface section has an orientation with a component in distal direction. The noncoverage by the insulating body may be restricted in particular to those regions of the electrode whose closest edge surface section is a section of the front surface of the electrode.

The insulating body may be made of one part or of multiple parts. Parts of the insulating body may be connected to each other or the parts are separate, spaced apart. Preferably, the insulating body consists of a seamless single piece. The electrode may be arranged in a recess in the insulating body, or the electrode may be arranged, for example, between two not-connected halves of the insulating body, said halves being able to two-dimensionally cover sections of the upper side and the underside of the electrode.

Preferably, the insulating body consists of a polymer, in particular a plastic material, for example silicone. Preferably, the insulating body is flexible in order to allow a bending of the distal end section of the instrument. The insulating body covers surface section of the electrode in order to prevent that the tissue of the covered surface sections is charged with surgically effective or damaging electrical output. For example, an undesirable drying-out of the tissue sections can be prevented in this manner. From the surface sections not covered by the insulating body, it is possible to apply an electrical output to the tissue in a surgically effective manner.

In preferred embodiments the insulating body is manufactured by overmolding the electrode. Preferably, a core is arranged, during the manufacture of the instrument according to the invention, in an exterior form next to the electrode and/or next to the electrode shaft—preferably at a distance—along the electrode and/or the electrode shaft, said core leaving at least sections of the channel free or forming at least sections of the channel while the electrode is being overmolded. There remains a channel within the wall thickness of the insulating body enclosing the electrode.

Preferably, the electrode has recesses, in particular holes, for fastening the insulating body to the electrode. If the insulating body is fabricated by casting, in particular injection molding, the cast material may penetrate through the holes and solidify in the holes, so that a positive lock is produced between the insulating body and the electrode.

Preferably, the electrode is held in an electrode shaft, wherein the insulating body may surround at least one distal end section of the electrode shaft in order to electrically insulate said shaft. The wire-shaped body may be fastened in or on the electrode shaft, in particular be inserted in the electrode shaft.

The channel extends next to the electrode shaft or, for example, in sections concentrically with the electrode shaft.

The instrument may have a handle in which the electrode shaft is supported so as to be rotatable, and the user can adapt the angular position of the electrode relative to the handle. If the channel extends concentrically with respect to the electrode shaft, the channel may be connected centrally—via a gas, fluid and/or aerosol line—to the gas, fluid and/or aerosol source.

Furthermore disclosed is a device which comprises an instrument according to the invention and a gas, fluid and/or aerosol source, wherein the channel of the instrument is connected to the gas, fluid and/or aerosol source in order to supply the channel with gas, liquid and/or aerosol.

BRIEF DESCRIPTION OF THE DRAWINGS

Additional preferred features and embodiments of the instrument according to the invention and the device according to the invention can be inferred from the description and the dependent claims, as well as from the figures. They show in FIG. 1—a perspective view of an exemplary embodiment of an instrument according to the invention, FIG. 2—a plan view of the distal end of the instrument according to FIG. 1, FIG. 3—a perspective view of the instrument according to FIG. 1, with the position of the electrode and the channel indicated in dashed lines, FIG. 4—an exemplary electrode assembly with the electrode shaft and the electrode of the instrument according to FIG. 1, FIG. 5—a detail of a section of a longitudinal sectional view of the instrument according to FIG. 1, along the longitudinal axis of the electrode, FIGS. 6a, 6b—plan views of exemplary embodiments of distal spatula sections, FIG. 7a—a perspective view of the distal end section of an example of a further embodiment of the instrument according to the invention, FIG. 7b—a representation of a longitudinal section of the example according to FIG. 7a, FIG. 8a—a perspective representation of an example of a third embodiment of the instrument according to the invention, FIG. 8b—a plan view of the upper side of a further example according to a third embodiment of the instrument according to the invention, FIG. 8c—a perspective representation of yet a further example according to the third embodiment of the inventive instrument.

DETAILED DESCRIPTION

Figure 1:
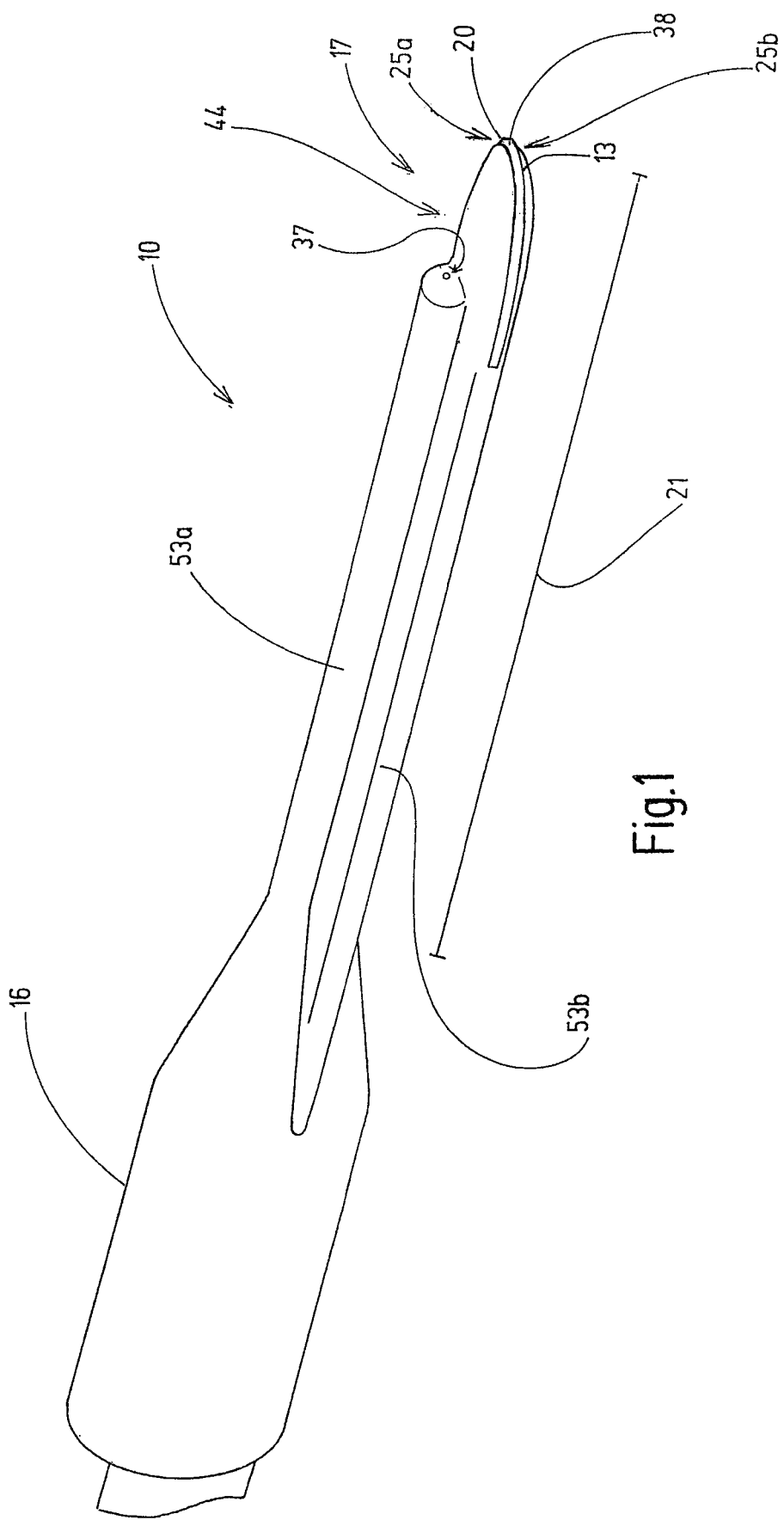
Figure 2:
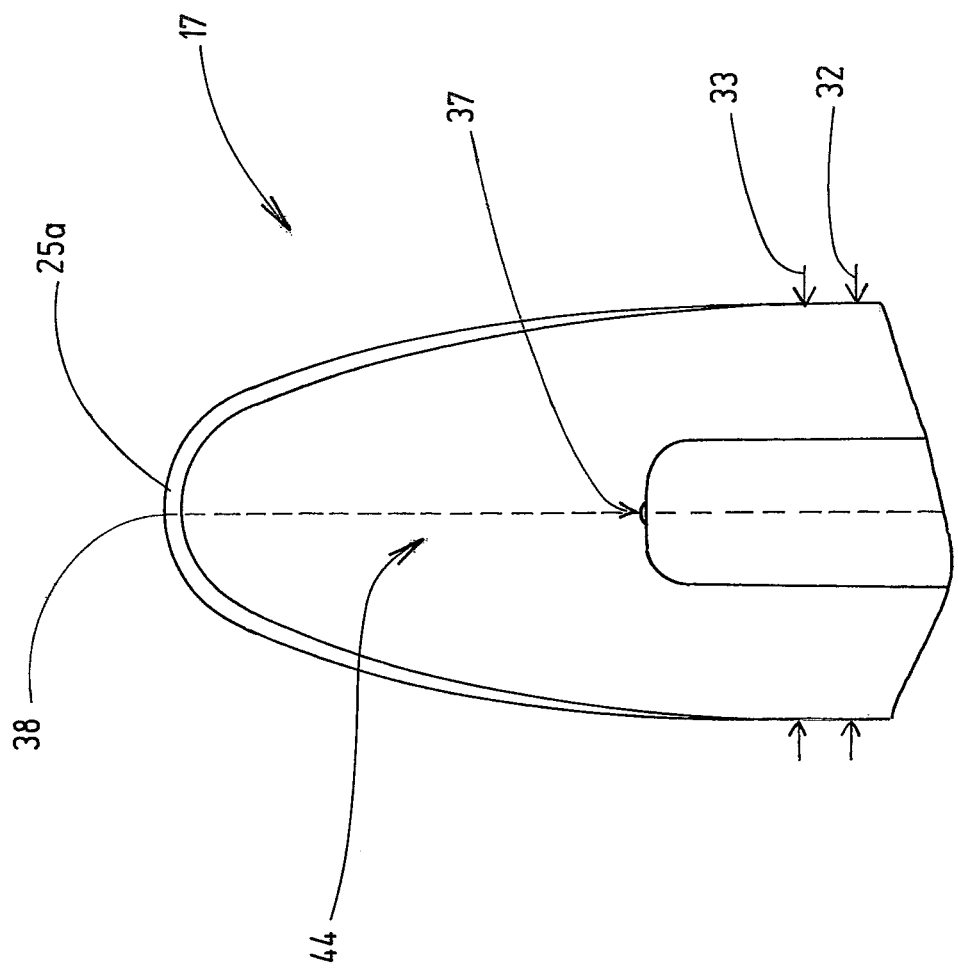

FIGS. 1 to 5 shows details of an example of a preferred structure of a preparation instrument 10 according to the invention in one embodiment according to the invention. The preparation instrument 10 comprises an electrode assembly 12 (see in particular, FIGS. 3 and 4) with an electrode 13 and an electrode shaft 14, wherein the electrode 13 is held in the electrode shaft 14. The proximal end of the electrode shaft 14 may be releasably inserted in a handle (not shown) of the instrument 10. The electrode assembly 12 may be rotatably supported in the handle so as to be able to adapt the orientation of rotation of the electrode assembly 12 around the longitudinal axis of the electrode shaft. Via the electrode shaft 14, the electrode 13 is electrically connected to an HF-generator (not illustrated). The electrode 13 is enclosed by an insulating body 16, which partially insulates the electrode 13. This means that the insulating body 16 covers the insulated sections of the electrode 13 in order to prevent that the tissue is charged transversely through the surface of the insulated sections with a surgically effective—in particular, cutting—or damaging electrical output. The insulating body 16 covers the surface sections of the electrode 13 or adapts to the surface sections of the electrode 13, preferably in a two-dimensional manner, in order to insulate said electrode. The insulating body 16 preferably encloses at least the end of the electrode shaft 14 and extends from there to the working tip 17 of the instrument 10, where the insulating body 16 leaves an edge region 20 of the electrode 13 exposed. The preparation instrument 10 has an end section 21 which extends from the electrode shaft 14 to the distal end of the preparation instrument 10.

The electrode 13 has the form of a spatula with an upper side 22a and an underside 22b facing in the opposite direction. The upper side 22a and the underside 22b are laterally connected to each other via one lateral surface 23a, b on each side and distally to a front surface 24 adjacent to the lateral surfaces 23a, b. The lateral surfaces 23a, b and the front surface 24 form an edge surface of the electrode 13.

Preferably, the front surface 24 is completely or at least partially not insulated. The lateral surfaces 23a, b are preferably insulated up to the front surface 24. Preferably, the electrode 13 projects distally from the insulating body 16. Preferably, the electrode 13 projects from the insulating body 16 adjacent to the front surface 24.

On the lateral surfaces 23a, b and/or on the front surface 24, the electrode 13 is preferably free of recesses that are open toward the lateral surfaces 23a, b or the front surface 24, said recesses potentially forming a hook shape of the electrode 13, for example.

Particularly preferably, an arcuate (has the form of a curved strip) section 25a of the upper side 22a adjoining the front surface 24 and/or such a section 25b of the underside 22b is not insulated, wherein the section or sections 25a—in plan view of the upper side 22a and/or the underside 22b—enclose the insulating body 16. The strip-shaped section or sections 25a, b adjoin the front surface 24. The strip-shaped section or sections 25a, b may have a width B of 0.05 millimeters to 2 millimeters, for example. In the exemplary embodiments according to FIGS. 6a and 6b, the strip-shaped section has a width B of 0.1 mm to 0.15 mm, for example.

Preferably, the electrode 13 is continuously enclosed by the insulating body, from its proximal end 28 to the free strip-shaped section 25a, b. A section of the front surface 24 adjoins the surface section 29 of the electrode 13 that is enclosed up to there, said section being not covered continuously around the distal end 38 of the electrode 13 up to back to the enclosed surface section 29.

The width of the end section 21 of the preparation instrument 10 is preferably defined by the width 32 of the insulating body 16. Preferably, the electrode 13 ends with the insulating body 16 or has a smaller width 33 than the insulating body 16.

Inside the insulating body, in the wall which encloses the electrode 13, there extends a channel 35 along the electrode 13. The channel 35 and the electrode 13 extend preferably next to each other with a space (as illustrated) or without a space between the channel 35 and the electrode 13. On the distal end 36 of the end section 21, the channel 35 has an outlet 37. For example, the outlet 37—measured parallel to the electrode 13—may be between at least 2 millimeters up to including 10 millimeters set back, for example between including 2 millimeters to including 4 millimeters.

Figure 3:
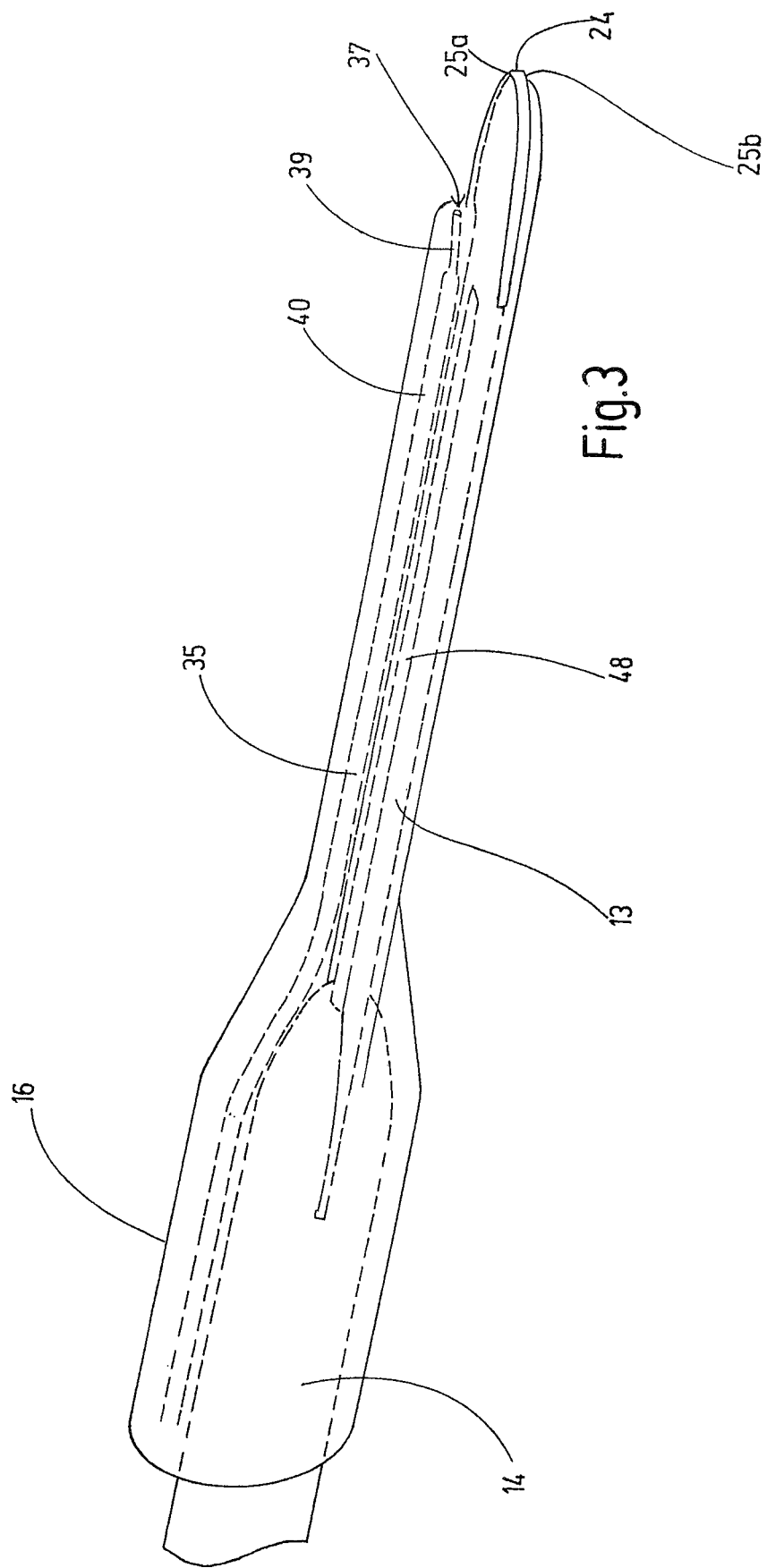
Figure 4:
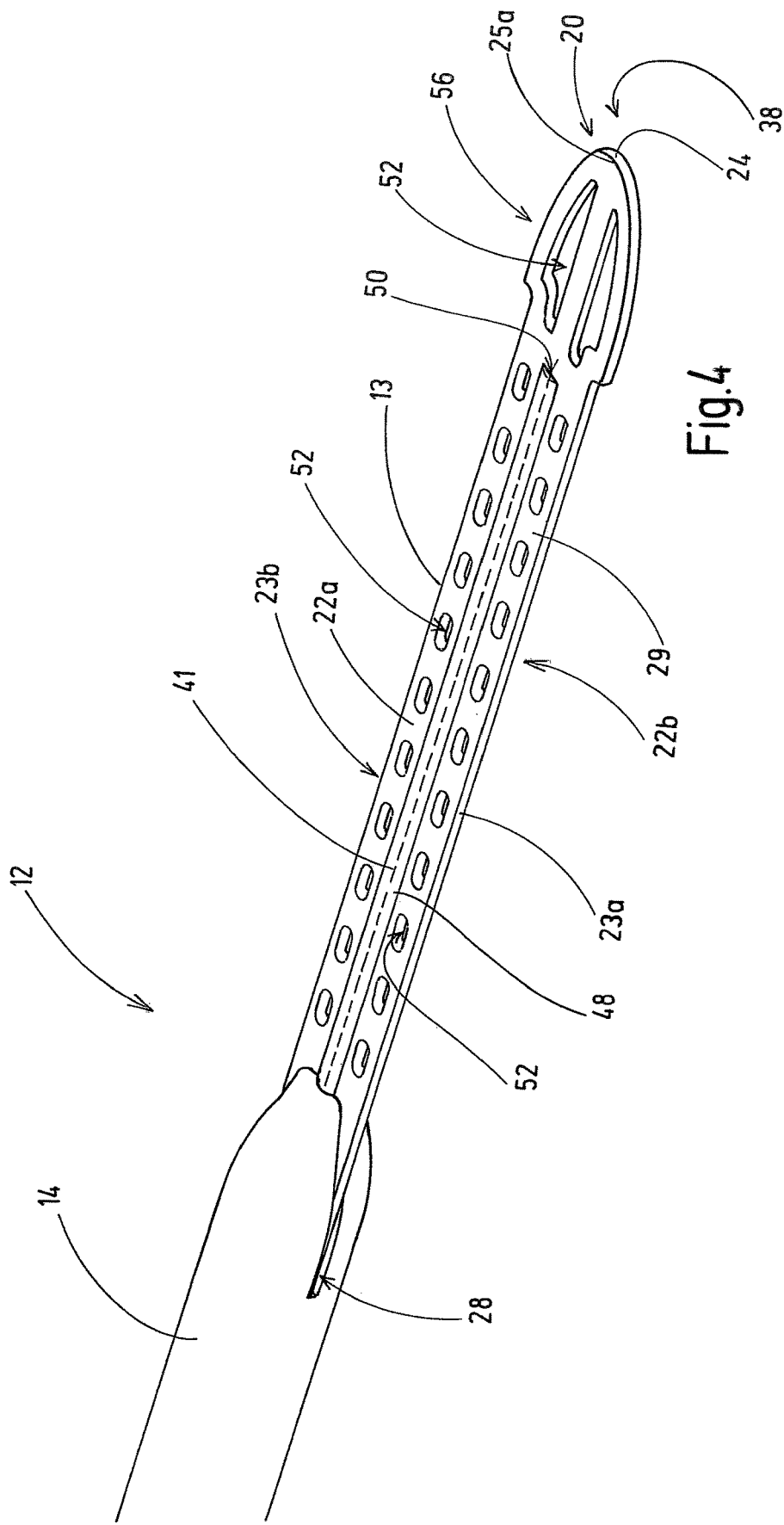
Figure 5:
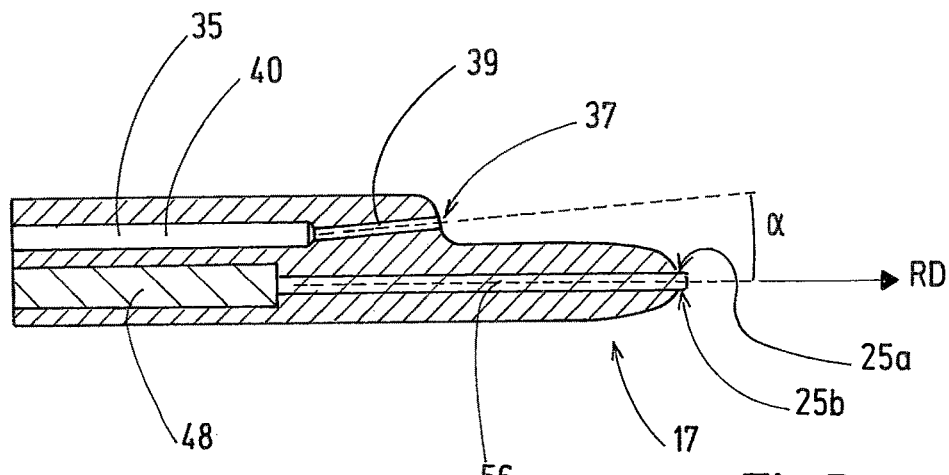

The channel 35 is arranged in the insulating body 16 according to the depicted embodiment adjacent to the upper side 22a or, for example, adjacent to the underside 22b (not illustrated) in the insulating body 16. It is also possible for one channel or one branch of a channel each to be arranged adjacent to the upper side 22a and adjacent to the underside 22b (not illustrated). A channel may be arranged adjacent to the other side, the underside 22b or the upper side 22a. The channel 35 extends in parallel direction (as illustrated by FIG. 3) or at least in sections concentrically (not illustrated) to the electrode shaft 14—initially along the electrode 13 (with a straight electrode 13 parallel to the electrode 13), wherein, preferably, a straight end section 39 of the channel 35 is angled relative to the electrode 13, so that the angle D D that is enclosed by the longitudinal axis of the end section 39 of the channel 35 and the longitudinal axis 41 of the electrode 13, opens in distal direction RD. The angle D is shown in FIG. 5 which illustrates a longitudinal sectional view through the distal end section of the instrument 10. The corresponding sectional plane intersects the paper plane in FIG. 2, perpendicularly along the intersection line indicated in dashed line in FIG. 2. The distal end section 39 of the channel 35 is preferably angled with respect to the longitudinal axis 41 of the section of the electrode 13 or with respect to the insulating body 16 that is arranged in the direction of flow of the fluid from the outlet 38 downstream of the outlet 37, preferably at an angle Q greater than 0° and up to 450, particularly preferably greater than 5° to smaller than 25°, for example 15±3°. If the channel 35 is supplied with liquid or aerosol, the liquid or aerosol flows out of this outlet 37 of the channel, for example in the form of a cone, for example a full cone. For example, the cone may have an opening angle (cone angle) of approximately 20°. Due to the orientation of the distal end section 39 of the channel 35, the cone may be oriented in such a manner that the cone does not contact the section of the insulating body 16 or the electrode 13 between the outlet 37 of the channel 36 and the distal end 38 of the electrode 13 or the instrument 10. In the exemplary embodiments, the fluid cone may be oriented in such a manner that the spray cone "surface" is approximately parallel or tangential to the surface of the section 44 of the instrument 10, said section extending from the outlet 37 of the channel 35 to the distal end of the instrument 10. If, however, the jet cone were to impinge upon the section 44, this can lead to a considerable, uncontrolled drop formation (accumulation of liquid at the electrode tip) and could negatively influence the electrical properties of the spatula, on the one hand, because, due to this accumulation of conductive liquid at the tip of the instrument, the effective contact surface of the electrode may be enlarged and thus the accumulation can counteract the objective of a precise (insulated) preparation and, on the other hand, restrict the view of the operating field.

As is shown in FIG. 3 and, in particular, in FIG. 5, the distal end section 39 of the channel 35 is preferably oriented parallel along a plane, or located in the plane which is perpendicular to the upper side 22a or the underside 22b of the electrode and which extends in longitudinal extent direction of the electrode 13, the wire-shaped section or body 48 or the insulating body that is arranged in the direction of flow of the fluid from the outlet 37 downstream of the outlet 37. The azimuth between the distal end section 39 of the channel 35 and the longitudinal extent direction of the electrode 13 and/or the wire-shaped section or body 48 and/or the longitudinal axis of the section of the electrode 13 or the insulating body 16 that is arranged in the direction of flow of the fluid at the outlet 37 downstream of the outlet 37, preferably is 0°, wherein the azimuth is measured between the vertical projection of the longitudinal axis of the distal end section 39 of the channel 35 on a plane, in which the spatula-shaped electrode 13 is located or can be bent in such a manner that it is located in this plane, and/or in which a section of the insulating body 16 or the electrode 13 is located, which section is arranged between the outlet 37 of the channel 35 and the distal end of the insulating body 16 and/or the electrode 13, and the longitudinal extent direction of the electrode 13 and/or of a wire-shaped body 48 or section, and/or the longitudinal axis of the section of the electrode 13 or the insulating body 16 which is arranged downstream as viewed in the direction of flow of the fluid from the outlet 37.

The distal end section 39 of the channel 35 is preferably a nozzle section having a flow cross-section that is smaller than the flow cross-section of the channel section 40 that is proximally adjacent to the distal end section 39. The proximally adjacent channel section 40 preferably has a diameter of 1 millimeter or less, e.g., about 0.6 millimeters.

The distal end section 21 of the instrument 10 with the insulating body 16 and the electrode 13 is preferably flexible, bendable with the bare hand and—after bending— preferably remains in the shape desired by the user. The end section 21 of the instrument 10 consequently can be bent— in particular from a straight orientation of the electrode 13 and the insulating body 16—in directions to adapt the shape of the end section 21 of the instrument 10 to the surgical task.

For a particularly precise orientation of the end section 21 of the instrument 10 by manually bending it, the channel 35 preferably is formed by a hollow space left open in the insulating body 16. As illustrated, the hollow space extends next to and preferably at a distance from the space in the insulating body 16, said space being filled by the electrode 13. Accordingly, the insulating body 16 preferably forms the wall delimiting the channel 35. The wall that delimits the channel 35 is preferably configured so as to be seamless in one piece with the insulating body 16. Alternatively or additionally, the distal end section 39, in particular the nozzle section, of the channel is preferably formed by a hollow space left open in the insulating body 16.

Preferably, the instrument 10 is adapted such that the orientation of the nozzle section 39 may be maintained at the time of bending, relative to the distal electrode section 38 and/or relative to the longitudinal axis 41 of the section of the insulating body 16 and/or the section of the electrode that is arranged—viewed in the direction of flow of the fluid through the channel 35—downstream of the outlet 37 (distal to the outlet 37). This is ensured by configuring the nozzle section 39 in the region of the distal end section 21 of the instrument 10, said section being held by the user for bending the distal end section 21, and in which, consequently, no bending moment occurs. Consequently, bending of the distal end section 21 of the instrument 10 always occurs proximally to the nozzle section 39. In particular, the distance between the outlet 37 and/or the nozzle section 39 and the distal end 38 of the electrode may be selected small enough that, while bending the end section 21, the bending of the distal end section 21 of the instrument 10 is always securely proximal to the nozzle section 39.

Alongside the electrode 13 there is preferably arranged a wire-shaped body 48, preferably of metal. The electrode 13 may have a longitudinal slit or cutout which may extend, for example, in longitudinal extent direction of the electrode from the proximal end 28 of the electrode 13 up to the distal end 38 of the electrode 13, in which case the wire-shaped body 48 is arranged in the slit or the cutout and is able to fill the cutout, as illustrated. Alternatively, the electrode 13 may, for example, have a wire-shaped section that is arranged centrically in the electrode 13—in the spatula form. The wire or wire-shaped section is disposed for stabilizing the distal end section 21 of the instrument 10 after being bent in the desired orientation, into which the distal end section 21 is brought by bending. The wire also is adapted for stabilizing the distal end section 21 in the starting configuration before being bent, so that a mechanical manipulation of the tissue is possible without increasing the thickness of the end section 21 of the electrode 13. The latter would lead to a worsening of the electrical properties of the RF-energy input, because, with a thicker electrode 13, the precision with which preparation is possible is less than with a thinner electrode 13.

The wire-shaped section or body 48 preferably ends in front of the distal end 38 of the electrode 13, so that a region between the distal end 50 of the wire-shaped body 48 and the distal end 38 of the electrode 13 is free of the wire-shaped section or body 48.

The electrode 13 itself and/or the wire-shaped body or section 48 preferably do not form or contain a fluid channel.

The electrode 13—with or without wire-shaped section— can be manufactured by means of a punching process, or photochemical etching or laser cutting.

In particular, the insulating body 16 may consist of polymer, in particular plastic, for example silicone. The insulating body 16 is formed preferably by overmolding—in particular overmolding by an injection-molding process—of the electrode 13 and of the electrode shaft 14 with insulating body material. Preferably, the channel 35 is produced as a hollow space in the insulating body 16 by molding by means of a core. In doing so, it is not necessary to arrange one or more capillary tubes or tubing that would result in greater mechanical stiffness in the insulating body 16, in which case the capillary tubes or tubing enclose the channel. As a result of this, the distal end section 21 of the instrument 10 with the electrode 13 and the end section 39 of the channel 35 can precisely oriented by bending, without the bending causing the orientation of the fluid jet leaving the outlet 37 of the channel 35 to change relative to the orientation of the distal end 38 of the electrode 13. The distal end section 39, in particular the nozzle section of the channel 35 may also be made so as to be an integral part, i.e., as an open volume in the insulating body 16. Due to this, an additional component such as, e.g., a nozzle tube, can be omitted. This is in particular of advantage for the assembly of embodiments of instruments 10 according to the invention. During the casting or injection molding process the insulating body 16 is preferably formed around the electrode 13 so that the electrode 18 is enclosed by the insulating body 16. Between the insulating body 16 and the electrode 13, for example between a silicone body as the insulating body 16 and the electrode 13, there is preferably no interlayer. Preferably, there is no bonding layer or any other bonding agent between the insulating body 16 and the electrode 13, for example between a silicone body as the insulating body 16 and the electrode 13.

The electrode 13, in particular the sections of the electrode 13 alongside the wire 48 or the wire section, preferably has recesses 52, in particular holes 52, which recesses 52 are filled with insulating body material during the manufacture of the insulating body 16, in order to form a positive lock between the insulating body 16 and the electrode 13, so that the insulating body 16 remains connected in positive locking manner also when the electrode 13 with insulating body 16 is being bent, and thus always displays a specific orientation relative to the electrode 13.

The longitudinal section 53a of the insulating body 16 that contains the channel 35 is preferably narrower than the adjacent longitudinal section 53b of the insulating body 16 that contains the electrode 13. This, too, promotes the precise bendability of the insulating body 16. The longitudinal section 53b of the insulating body that contains the electrode 13, in particular the region between the outlet 37 of the channel 35 and the distal end of the instrument 10 or the electrode 13, preferably also has the form of a spatula as illustrated.

As shown by FIG. 3, the channel 35 may extend next to the electrode shaft 14. In other embodiments, the channel 35 may be arranged concentrically inside the electrode shaft (not illustrated). This is particularly advantageous when the rotatability of the distal end section 21 of the instrument 10 about the longitudinal axis of the electrode shaft 14 relative to the handle is to be provided, so that the user is able to adapt the orientation of rotation of the distal end section 21 of the instrument 10 relative to the handle, as desired by the user.

Figures 6A, 6B:
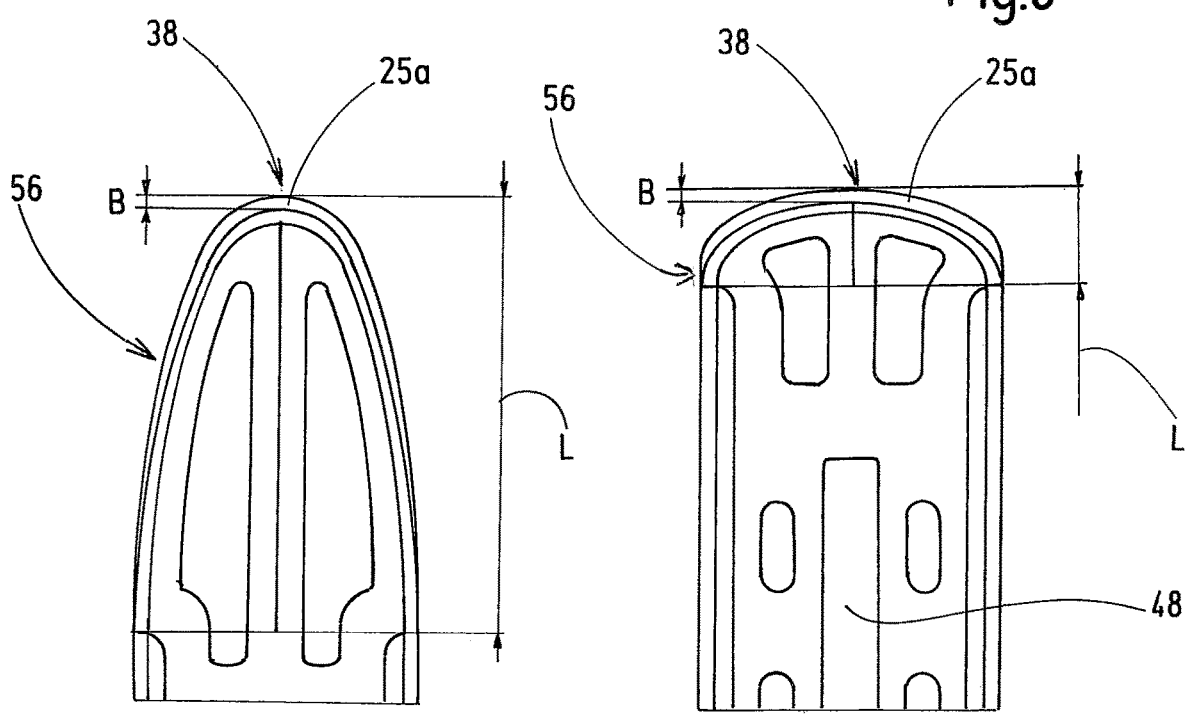

As is shown by FIG. 6a with reference to an example, the contour of the electrode 13 transitions in some embodiments from the distal end 38 of the electrode 13 into the sides of the electrode, without forming forward-oriented (distal) rounded corners. In contrast, FIG. 6b shows an example of an embodiment that forms such rounded corners 55a, b.

The lateral contour of the electrode tip 56 may taper toward the distal end 38 of the electrode (pointed profile, see FIGS. 2, 4, 6a), extend largely in parallel direction (rectangular profile, see FIG. 6b) or also widen (trapezoid profile, not illustrated). In doing so, the exposed section of the edge surface of the electrode may either be continuous (over the entire circumference of the spatula-shaped distal end section 21 of the instrument 10) or be limited to a distal portion of the preferably spatula-shaped distal end section 21 of the instrument 10.

The width of the electrode defined by the front surface transitions at the transition to the lateral surfaces and/or at the transition from the exposed region of the upper side 22a and/or the underside 22b to the not exposed region, preferably abruptly, into a smaller width, which is defined by the distance of the lateral surfaces 23a, b from each other. In the embodiments having an pointed profile (cf. FIGS. 2, 4, 6a) the transition from the distal end 38 of the electrode 13, measured in longitudinal extent direction of the electrode 13, may have a distance, for example, corresponding to at least the width 32 of the insulating body 16 in the end section 21 of the instrument 10 and/or corresponding to at least the greatest width 33 of the electrode 13 in the distal end section 21 of the instrument 10.

In the embodiments having a rectangular profile (cf. FIG. 6b) the transition from the distal end 38 of the electrode 13, measured in longitudinal extend direction of the electrode 38, may have a distance, for example, of at most one third of the width 32 of the insulating body 16 in the end section of the instrument 10 and/or the greatest width 33 of the electrode 13 in the distal end section 21 of the instrument 10.

The length L of the exposed region of the electrode 13 may be, for example, up to twice the width 32 of the end section 21 of the instrument 10, wherein the length L is measured in the longitudinal extent direction of the electrode 13. The length of the not covered region may be, e.g., 4.5 mm or less.

The channel 35 is preferably connected to a pump or a pressure source in order to supply the channel with gas, fluid and/or aerosol.

The instrument 10 according to the invention is manufactured, for example, as follows:

In an exterior form (not illustrated), an electrode assembly 12 having an electrode shaft 14 and an electrode 13 is provided, and, next to the electrode 12 and the electrode shaft 14—preferably at a distance from the electrode 12 and the electrode shaft 14—there is arranged an interior elongated form (elongated core) (not illustrated). Insulating body material is injected into the exterior form, so that it forms the insulating body 16 around the electrode shaft 14 and the electrode 13. The elongated core ensures that the channel 35 is left open in the insulating body 16.

The instrument according to the invention operates, for example, as follows:

The instrument 10 according to the invention can be used, for example, in open or in laparoscopic or endoscopic surgery. For HF-surgical treatment, in particular the preparation of tissue, an HF-output is applied to the electrode 13 and can then be used as a cutting tool for cutting tissue. The dispensing of a fluid, in particular an aerosol jet, from the outlet 37 of the channel 35 can be activated automatically, for example, with the activation of the application of the electrode 13 with an HF-output. In the embodiments, the dispensing of a fluid jet, in particular an aerosol jet, can be activatable, for example, independent of the activation of the HF-power output by the electrode 13.

With the use of the preparation instrument 10 according to the invention, in which an HF-spatula (spatula-shaped electrode 13) is combined with a fluid applicator 38) (pump or pressure source and channel), in particular an aerosol applicator (hybrid spatula), it is possible—by dispensing a fluid, in particular a fluid jet or aerosol jet—to improve the view of the surgical site and thus allow more precise and safe work. With the instrument 10 according to the invention, it is possible to gently and precisely prepare tissue. The instrument 10 according to the invention helps the user prevent inadvertent thermal damage to sensitive (to be prepared) or adjoining structures because dispensing of the fluid jet, in particular the fluid jet and aerosol jet, allows the preparation—by cleaning or preparation—of the surgical site, so that the contact surface between the tissue and the HF-electrode 13 is known to the user at all times or is controllable by the user, and, in addition, the individual tissue boundaries are clearly recognizable at all times by the surgeon using the instrument 10. Preferably, the instrument 10 is adapted for applying a gas, a fluid or a mixture of both (aerosol) to the tissue (tissue displacement) in order to, among other things, rinse away blood and present individual tissue structures or their boundaries more clearly. Alternatively or additionally, the instrument 10 may be adapted for introducing liquid or aerosol into the tissue in order to elevate a tissue layer (tissue elevation).

During the application of a fluid (in particular a liquid) having a high output density, the fluid penetrates the tissue and accumulates in the connective-tissue-like boundary regions between the target structure and the adjacent structures, so that they are forced apart and an enlarged (safety) distance for the manipulation with the instrument 10 is formed (mechanical and thermal protection).

If, however, with the use of an instrument 10 according to the invention, a fluid stream (in particular a gas or aerosol) displaying relatively low intensity is directed at the tissue at a certain distance, there will be displacement effects (deformation) on the tissue due to the effect of the force of the flowing fluid. Due to various mechanical properties, e.g., the elasticity of the individual tissue structures, this may be more or less pronounced. Consequently, stiffer structures such as, for example, vessels, can be more clearly defined with respect to the surrounding softer tissue such as, e.g., fat.

Due to the application of an aerosol spray, it is furthermore possible to implement a cooling of the surgical site and thus an additional protection against thermal damage due to influence of high frequency power.

Finally, the aerosol dispensed with the use of the channel 35 of the instrument according to the invention allows the reduction of smoke formation during HF-application in order to thus provide a clearly improved view of the surgical site.

With an outlet 37 of the channel 35 that is proximally set back from the distal end 38 of the electrode 13, the risk of damage to the tissue by the aerosol is avoided and/or a dispensing of the aerosol into the tissue, e.g., a blood vessel, is prevented. In particular, as a result of this, a setting of the outlet 37 of the channel 35 onto the tissue is prevented.

Consequently, with the instrument 10 according to the invention a demand for a preparation instrument has been met, which instrument allows a precise and gentle exposure/presentation of sensitive tissue structures.

Preferably, as described hereinabove, the user can bend the end section 21 of the instrument 10 by hand, so that the orientation of the nozzle section 39 relative to the distal electrode section 38 and/or relative to the longitudinal axis 41 of the section of the insulating body 16 and/or the longitudinal axis 41 of the section of the electrode 13, which, viewed in the direction of flow of the fluid through the channel 35, is arranged downstream 37 of the outlet 37 (distal to the outlet 37) remains maintained.

FIG. 7a and FIG. 7b show an example of a further embodiment of the instrument 10 according to the invention. This embodiment has a spatula-shaped electrode 13 that may have a longitudinal cutout in which a wire-shaped body 48 is arranged, or which, for example, has a central wire-shaped section. Different from the embodiment according FIGS. 1 to 5, the channel 35 is arranged in the insulating body 16 adjacent to a narrow lateral surface 23a of the electrode 13 and not, as in the exemplary embodiments according to FIGS. 1 to 5, adjacent to the wider upper side 22a of the electrode 13. The end section 39 of the channel 35 can—different than illustrated—be arranged at an angle α relative to the longitudinal extent direction of the distal end section 21 or the electrode 13, so that the angle opens in distal direction. In the depicted exemplary embodiment, the end section 39 of the channel 35 extends parallel to the longitudinal extent direction of the electrode 13 or the longitudinal extent direction of the distal end section 21, respectively. The electrode 13 may have a hook cutout 60 on one or both lateral surfaces 23a, b. The region 61 of the electrode 13 that is not covered by the insulating body 16 inside the hook cutout 62 of the insulating body 16 can be impacted by the gas, aerosol or liquid jet in order to clean same. Alternatively or additionally, a jet from the channel 35 can be applied to the tissue which is to be treated within the hook-shaped cutout 60, 62, previously or at the same time.

Alternatively or additionally, by applying a gas, aerosol or liquid jet to the tissue that is in contact with the distal end of the electrode 38, it is possible to produce displacement effects (deformation). As a result of this, individual structures can be limited more clearly relative to each other. In the insulating body 16, there may be arranged an evacuation channel 63. Like the channel 35 for dispensing a gas, liquid, aerosol jet to or into the tissue or between tissue structures, the insulating body 16 may also form the channel wall of an evacuation channel 63. The electrode 13 projects laterally beyond the insulating body 16, so that the width 64 of the section of the instrument 10 is defined between the outlet 37 of the channel 35 and the distal end of the instrument 10 by the electrode 13 and the insulating body 16.

FIGS. 8a and 8b show examples of embodiments, in which the channel 35 is formed in the electrode 13. The channel 35 that is integrated in the electrode 13 may have an outlet 37 on the distal end of the instrument 10. The electrode 13 may not project distally, as well as laterally, beyond the insulating body 16 (FIG. 8a), but end with the insulating body 16, so that only the lateral surface section 63 is not covered by the insulating body 16. Otherwise, the electrode 13, for example, the electrode 13 may not project distally beyond the insulating body 16, but only lateral sections 64 of the upper side 22a and/or the underside 22b of the electrode 13 may not be covered by the insulating body 16, as illustrated. Furthermore, the depicted exemplary embodiments are different in that, in FIG. 8a, only one lateral surface 23a of the instrument 10 has a hook through a recess 60, 62 in the insulating body 16 of the electrode 13, and in FIG. 8b both lateral surfaces 23a, b have a hook.

The example according to FIG. 8c differs from the example according to FIG. 8a in particular in that the electrode 13 in the hook recess 62 of the insulating body 16 projects distally, and also laterally, beyond the adjoining contour of the insulating body 16.

The insulating body may have a recess (not illustrated) through which a two-dimensional section of the electrode may be exposed for coagulating in order to form a coagulation region. As an alternative to being exposed, a coagulation region may be formed (not illustrated), in that a section of the insulating body may display a porosity that is adapted in such a manner that the insulating body in this section does not insulate the electrode in order to allow the application of an electrical output to the tissue for coagulation of the tissue through this section.

Disclosed is a preparation instrument 10 (hybrid instrument) which comprises an HF-instrument with an electrode 13 that is partially insulated by means of an insulating body 16, which is combined with a fluid applicator having a channel 35 arranged in the insulating body 16 for the application of a fluid to or into tissue. In particularly preferred embodiments of the preparation instrument 10, the electrode 13 is a spatula electrode which is inserted in the insulating body 16 that does not cover sections 24, 25a, 25b, 63, 64 of the surface of the electrode 13, so that these sections 24, 25a, 25b, 63, 64 may be in contact with the tissue. In the particularly preferred embodiments, the insulating body 10 preferably forms the channel wall that delimits the channel 35. In the particularly preferred embodiments, the insulating body 16 and the electrode 13 are flexible in order to adapt the form of the insulating body 16 and the electrode 13, together, to the surgical task.

LIST OF REFERENCE SIGNS

| | |
|---|---|
| 10 | Preparation instrument/instrument |
| 12 | Electrode assembly |
| 13 | Electrode |
| 14 | Electrode shaft |
| 16 | Insulating body |
| 17 | Working tip |
| 20 | Edge region of the electrode |
| 21 | End section |
| 22a | Upper side |
| 22b | Underside |
| 23a, b | Lateral surfaces |
| 24 | End surface |
| 25a, b | Sections |
| 28 | Proximal end of the electrode |
| 29 | Surface section |
| 32 | Width of the insulating body |
| 33 | Width of the electrode |
| 35 | Channel |
| 36 | Distal end |
| 37 | Outlet of the channel |
| 38 | Distal end of the electrode |
| 39 | End section of the channel/nozzle section |
| 40 | Proximal adjacent end of the channel |
| 41 | Longitudinal axis of the electrode |
| 44 | Section of the instrument |
| 48 | Wire-shaped body |
| 50 | Distal end of the wire-shaped body/section |
| 52 | recess |
| 53a, b | Longitudinal sections |
| 55a, b | Corners |
| 56 | Electrode tip |
| 60 | Hook cutout |
| 61 | Region |
| 62 | Hook cutout |
| 63 | Lateral surface section |
| 64 | Section |
| ☐ | Angle |
| RD | Distal direction |
| L | Length |
| B | Width |

The invention claimed is:

1. A high frequency (HF) surgical preparation instrument (10) for acting on tissue, the instrument comprising:
   an electrode (13) having a body with a flat configuration including opposing flat surfaces and an outer edge surface extending therebetween;
   an insulating body in contact with and extending over the opposing flat surfaces, wherein an entirety of the electrode body is covered by the insulating body except for at an uninsulated portion of the electrode body that protrudes from the insulating body;
   a channel (35) disposed within the insulating body (16) for dispensing a fluid, a gas or an aerosol, wherein the channel (35) is adapted to be connected to a fluid, gas and/or aerosol source;
   wherein the channel comprises a nozzle for dispensing the fluid, gas or aerosol onto or into the tissue;
   wherein the channel and nozzle are separate and spaced apart from the electrode such that the fluid, gas or aerosol supplied by the fluid, gas and/or aerosol source does not come into contact with the electrode prior to being dispensed from the nozzle;
   wherein the uninsulated portion of the electrode body comprises at least a portion of the outer edge surface;
   wherein an outlet of the nozzle is set back proximally from an endmost distal extent of the electrode body; and
   wherein the nozzle is configured to dispense the fluid, gas or aerosol from the outlet such that the fluid, gas or aerosol does not contact the uninsulated portion of the electrode body as it passes thereby.

2. The instrument (10) according to claim 1, wherein the insulating body (16) circumferentially delimits the channel (35).

3. The instrument (10) according to claim 1, wherein the channel has a nozzle section (39) that is circumferentially delimited by the insulating body (16).

4. The instrument (10) according to claim 1, further comprising a distal end section (21) of the instrument (10) that is bendable in order to adapt a form of the distal end section (21) to a treatment task.

5. The instrument (10) according to claim 1, wherein the outlet (37) of the nozzle is set back from the endmost distal extent of the electrode (13) by 2 mm to 10 mm.

6. The instrument (10) according to claim 1, wherein the uninsulated portion of the electrode (13) body projects distally from the insulating body (16).

7. The instrument (10) according to claim 1, wherein the electrode (13) body has the form of a spatula.

8. The instrument (10) according to claim 7, wherein the electrode (13) body has a wire-shaped section (48) or wherein the electrode (13) body has a cutout, in which a wire-shaped body (48) is arranged.

9. The instrument (10) according to claim 1, wherein the insulating body (16) is overmolded about at least a portion of the electrode (13) body.

10. The instrument (10) according to claim 1, wherein the electrode (13) body has through openings (52) through which the insulating body extends for fastening the insulating body (16) to the electrode (13) body.

11. The instrument (10) according to claim 1, wherein the electrode (13) body is held in an electrode shaft (14), wherein the insulating body (16) encloses a distal end section of the electrode shaft (14).

12. The instrument (10) according to claim 11, wherein the channel (35) extends next to the electrode shaft (14) or concentrically with the electrode shaft (14) along sections thereof.

13. The instrument (10) according to claim 1, wherein the uninsulated portion of the electrode (13) has an arcuate shape.

14. The instrument of claim 1, wherein the insulating body comprises a distal end and opposing lateral sides extending proximally therefrom, wherein the outer edge surface of the uninsulated portion of the electrode body extends along at least a portion of one of the opposing lateral sides of the insulating body.

15. An apparatus, comprising:
   a high-frequency (HF) surgical preparation instrument (10) for acting on tissue, the instrument comprising:
   an electrode (13) having a body with a flat configuration including opposing flat surfaces and an outer edge surface extending therebetween;
   an insulating body in contact with and extending over the opposing flat surfaces, wherein an entirety of the electrode body is covered by the insulating body except for at an uninsulated portion of the electrode body that protrudes from the insulating body;
   a channel (35) disposed within the insulating body (16) for dispensing a fluid, a gas or an aerosol, wherein the channel comprises a nozzle for dispensing the fluid, gas or aerosol onto or into the tissue; and
   a fluid source, a gas source and/or an aerosol source, wherein the channel (35) of the instrument (10) is connected to the fluid source, the gas source and/or the aerosol source for supplying the channel (35);

wherein the channel and nozzle are separate and spaced apart from the electrode such that the fluid, gas or aerosol supplied by the fluid source, gas source and/or aerosol source does not come into contact with the electrode prior to being dispensed from the nozzle;

wherein the uninsulated portion of the electrode body comprises at least a portion of the outer edge surface;

wherein an outlet of the nozzle is set back proximally from an endmost distal extent of the electrode body; and wherein the nozzle is configured to dispense the fluid, gas or aerosol from the outlet such that the fluid, gas or aerosol does not contact the uninsulated portion of the electrode body as it passes thereby.

16. The apparatus of claim 15, wherein the insulating body comprises a distal end and opposing lateral sides extending proximally therefrom, wherein the outer edge surface of the uninsulated portion of the electrode body extends along at least a portion of one of the opposing lateral sides of the insulating body.

* * * * *